(12) United States Patent
Lee et al.

(10) Patent No.: US 11,612,611 B2
(45) Date of Patent: Mar. 28, 2023

(54) COMPOSITION AND METHOD FOR TREATING MUSCLE CRAMPS CONTAINING CHOLINE ALFOSCERATE AS ACTIVE INGREDIENT

(71) Applicant: NANOSTEM CO., LTD., Gyeonggi-do (KR)

(72) Inventors: Kweon Haeng Lee, Seoul (KR); Jun-Ho Yeo, Gyeonggi-do (KR); Young Lim, Seoul (KR); Kunik Lee, Madison, WI (US); So Hee Hyun, Seoul (KR)

(73) Assignee: HUB WASHINGTON INC., Spokane, WA (US)

( * ) Notice: Subject to any disclaimer, the term of this patent is extended or adjusted under 35 U.S.C. 154(b) by 249 days.

(21) Appl. No.: 16/771,515

(22) PCT Filed: Nov. 26, 2018

(86) PCT No.: PCT/KR2018/014576
§ 371 (c)(1),
(2) Date: Jun. 10, 2020

(87) PCT Pub. No.: WO2019/117501
PCT Pub. Date: Jun. 20, 2019

(65) Prior Publication Data
US 2021/0169906 A1 Jun. 10, 2021

(30) Foreign Application Priority Data
Dec. 11, 2017 (KR) .................... 10-2017-0169325

(51) Int. Cl.
| | | |
|---|---|---|
| *A61K 31/685* | (2006.01) | |
| *A23L 33/10* | (2016.01) | |
| *A23L 33/00* | (2016.01) | |
| *A61P 21/02* | (2006.01) | |
| *A23L 2/52* | (2006.01) | |
| *A61K 9/00* | (2006.01) | |

(52) U.S. Cl.
CPC .............. *A61K 31/685* (2013.01); *A23L 2/52* (2013.01); *A23L 33/10* (2016.08); *A23L 33/40* (2016.08); *A61K 9/0019* (2013.01); *A61K 9/0056* (2013.01); *A61P 21/02* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 4,424,946 A | 1/1984 | Kramer | |
| 11,311,561 B2* | 4/2022 | Lee | A61K 9/2059 |
| 2009/0176740 A1 | 7/2009 | Phillips, II | |
| 2010/0311692 A1 | 12/2010 | Lee | |

| | | |
|---|---|---|
| 2012/0101069 A1 | 4/2012 | Moeddel |
| 2012/0135087 A1 | 5/2012 | Di Schiena |
| 2013/0018006 A1 | 1/2013 | King |

FOREIGN PATENT DOCUMENTS

| | | |
|---|---|---|
| EP | 0201623 | 11/1986 |
| KR | 1020140094679 | 7/2014 |
| KR | 1020170027684 | 3/2017 |
| KR | 1020170094667 | 8/2017 |
| KR | 1018643840000 | 5/2018 |

OTHER PUBLICATIONS

Ceda, G. et al. Alpha Glycerylphosphorylcholine Administration Increases the GH Responses to GHRH of Young and Elderly Subjects. Hormone and Metabolic Research 24(3)119-121, Mar. 1992. (Year: 1992).*
Kapoor, V. et al. Herbals in the Control of Ageing. Drug Discovery Today 14(19/20)992-998, Oct. 2009. (Year: 2009).*
Vega, J.A., et al., "Nerve Growth Factor Receptor Immunnoreactivity in the Cerebellar Cortex of Aged Rats: Effect of Choline Alfoscerate Treatment," Mechanisms of Ageing and Development, 69 (1993), 119-127.
Internet web page, "Alpha Glycerylphosphorylcholine/Piracetam" May 7, 2017, pp. 1-11, <https://www.tabletwise.com/medicine/alpha-glycerylphosphorylcholine-piracetam>.
Minetto et al., "Origin and Development of Muscle Cramps", Exercise and Sport Sciences Reviews, Jan. 2013, vol. 41, No. 1, pp. 3-10.
Allen et al., Nocturnal Leg Cramps:, Am Fam Physician, 2012, vol. 4, pp. 350-355.
Hensley, "Leg Cramps and Restless Legs Syndrome During Pregnancy", Journal of Midwifery & Women's Health, 2009, vol. 54, No. 3, pp. 211-218.
Baltodano et al., "Verapamil vs Quinine in Recumbent Nocturnal Leg Cramps in the Elderly", Arch Intern Med, 1988, vol. 148, pp. 1969-1970.
Voon et al., Diltiazem for nocturnal leg cramps, Letters to the Editor, Division of Cardiology, Department of Internal Medicine, 2001, pp. 91-92.
Stern, "Value of Carisoprodol (Soma) in Relieving Leg Cramps", Caraisoprodol for Leg Cramps, 1963, pp. 1008-1013.
Popkin, "Orphenadrine Citrate (Norflex) for the Treatment of 'Restless Legs' and Related Syndromes", Journal of the American Geriatrics Society, 1971, vol. 19, No. 1., pp. 76-79.

(Continued)

*Primary Examiner* — Ralph J Gitomer
(74) *Attorney, Agent, or Firm* — Duane Morris LLP; Gregory M. Lefkowitz; Brandon A. Chan

(57) ABSTRACT

Choline alfoscerate is a drug used to improve cerebrovascular diseases and brain metabolism. It is a drug with proven safety, which has no effect on the kidney and liver and with no severe side effect reported. When administered to a patient with muscle cramps, it can significantly reduce pain and the occurrence of muscle cramps. Accordingly, it may be used as an active ingredient in a pharmaceutical composition for treating or preventing muscle cramps and a health functional food composition for improving muscle cramps and may also be used for a method for treating muscle cramps by administering choline alfoscerate. In addition, choline alfoscerate may also be used to prepare a medication for treating muscle cramps.

3 Claims, No Drawings

(56) References Cited

OTHER PUBLICATIONS

Chan et al., "Randomized, Double-Blind, Placebo-Controlled Study of the Safety and Efficacy of Vitamin B Complex in the Treatment of Nocturnal Leg Cramps in Elderly Patients with Hypertension", Journal of Clinical Pharmacology, 199, vol. 38, pp. 1151-1154.
Guay, "Are There Alternatives to the Use of Quinine to Treat Nocturnal Leg Cramps?", The Consultant Pharmacist, 2008, vol. 23, No. 2, pp. 141-156.
Katzberg et al., "Assessment: Symptomatic treatment for muscle cramps (an evidence-based review)", Neurology, 2010, vol. 74, pp. 691-697.
Prateepavanich et al., "The Relationship Between Myofascial Trigger Points of Gastrocnemius Muscle and Nocturnal Calf Cramps", J. Med Assoc Thai, 1999, vol. 82, No. 5, pp. 451-459.
Kim et al., "The Effects of Myofascial Trigger Point Injections on Nocturnal Calf Cramps", JABFM, 2015, vol. 28, No. 1, pp. 21-27.
Park et al., "Botulinum Toxin Treatment for Nocturnal Calf Cramps in Patients With Lumbar Spinal Stenosis: A Randomized Clinical Trial", Archives of Physical Medicine and Rehabilitation, 2017, vol. 98, pp. 957-963.
Farrar et al., "Clinical importance of changes in chronic pain intensity measured on an 11-point numerical pain rating scale", Pain, 2001, vol. 94, No. 2, pp. 149-158.
Rowbotham, "What is a 'clinically meaningful' reduction in pain?", Pain, 201, vol. 94, pp. 131-132.
Hawker et al., "Measures of Adult Pain", Arthritis Care & Research, 2011, vol. 63, No. 11, pp. S240-S252.

* cited by examiner

COMPOSITION AND METHOD FOR TREATING MUSCLE CRAMPS CONTAINING CHOLINE ALFOSCERATE AS ACTIVE INGREDIENT

CROSS-REFERENCE TO RELATED APPLICATIONS

This application is a § 371 national stage entry of International Application No. PCT/KR2018/014576, filed on Nov. 26, 2018, which claims priority to South Korean Patent Application No. 10-2017-0169325, filed Dec. 11, 2017, the entire contents of which are incorporated herein by reference.

BACKGROUND

Field of the Invention

The present disclosure relates to a pharmaceutical composition for treating or preventing muscle cramps, a health functional food composition for improving muscle cramps, a method for treating muscle cramps and a novel use of choline alfoscerate for preparation of a medication for treating muscle cramps.

Background Art

Muscle cramps refer to sudden involuntary muscle contraction accompanied by cramping pain of skeletal muscles. Lasting from a few seconds to several minutes, the cramps occur in one muscle, most frequently in the calf and foot muscles, followed by the femoral and hamstring muscles. The muscle cramps resolve on their own over time and disappear quickly by stretching (Minetto 2013).

Muscle cramps occur in 37% of healthy adults every year and nocturnal leg cramps occur in 60% of adults (Allen 2012). 30% of pregnant women experience muscle cramps in legs (Hensley 2009).

The most common muscle cramps are paraphysiologic muscle cramps occurring in healthy adults in response to physiological stimulations. Exercise-associated muscle cramps (EAMC) occurring after exercise in healthy people, benign muscle cramps occurring in normal people without underlying diseases, pregnancy-associated muscle cramps, etc. belong to this category. In this case, no special examination is necessary. For other muscle cramps associated with underlying diseases, special examination is necessary for accurate diagnosis and the occurrence of muscle cramps can be reduced by treating the underlying diseases.

The muscle cramps must be distinguished from spasm, myoclonus, restless legs syndrome, etc. which show involuntary muscle contraction regardless of pain.

Stretching, massage, etc. of the muscles where muscle cramps occurred may be employed for non-drug treatment of the muscle cramps. In addition, stretching may be helpful in preventing muscle cramps.

For drug treatment of muscle cramps, the anti-malarial drug quinine had been used as the most effective therapeutic agent until its use as a therapeutic agent for muscle cramps was banned in 2006 by the USFDA due to the severe side effects (665 cases) including death (93 cases) and low platelet count reported since 1969.

As other drugs, verapamil (Baltodano 1988), diltiazem (Voon 2001), gabapentin, the muscle relaxants carisoprodol (Stern 1963) and orphenadrine (Popkin 1971), vitamin E (Chan 1998), magnesium, etc., which has much fewer side effects than quinine, have been suggested as therapeutic agents (Guay 2008, Katzberg 2010). However, they are difficult to be used as main therapeutic agents due to limited therapeutic effect and side effects and are inapplicable to large-scale clinical trials. Although there are some exceptional cases where they are used for muscle cramps associated with other diseases, such as verapamil used in patients with hypertension or arrhythmia, gabapentin used in patients with epilepsy or neuropathy and vitamin E used for dialysis-associated cramps, they cannot be used as primary therapeutic agents in general sense.

In addition to the drug medication, the therapeutic effect of injection of lidocaine, botulinum toxin, etc. into the calf muscle was confirmed for muscle cramps (Prateepavanich 1999, Kim 2015, Park 2017). When 1-2 mL of 0.25% lidocaine was administered to the myofascial trigger points (MTrPs) of the gastrocnemius muscle of patients with nocturnal calf cramps, 1) the intensity of pain, 2) the frequency of cramps for a week and 3) the insomnia severity index (ISI) decreased significantly as compared to before the administration (Kim 2015).

Choline, which is a precursor for the neurotransmitter acetylcholine, is one of very useful nutrients necessary for improving brain metabolism or enhancing mental ability. Choline alfoscerate (alpha-GPC), wherein a phospholipid component is bonded to choline, is a semisynthetic derivative of lecithin and is also known as L-alpha glycerylphosphorylcholine. Choline alfoscerate helps the conversion or synthesis of important neurotransmitters in the brain. Specifically, choline alfoscerate is degraded into choline and glycerophosphate after being absorbed in the body and is involved in the production of the neurotransmitter acetylcholine while it passes through the central nervous system (CNS) via the blood-brain barrier (BBB).

Accordingly, it is known that the administration of choline alfoscerate provides therapeutic effect for diseases with the symptoms of decreased neurotransmitters.

At present, choline alfoscerate is useful for treating cognitive dysfunction associated with cerebrovascular diseases and degenerative brain diseases. Especially in Alzheimer's disease, the combined treatment of cholinesterase inhibitor donepezil and choline alfoscerate decreases behavioral and cognitive disturbances more effectively than using donepezil only.

Although many people suffer from muscle cramps, a therapeutic agent for muscle cramps which is safe, effective and economical is not available yet. The inventors of the present disclosure have first identified that choline alfoscerate, which has been used to treat cognitive disturbances, exhibits an effect of suppressing muscle cramps in short time with few side effects and have completed the present disclosure.

REFERENCES OF RELATED ART

Patent Documents (Patent document 1) US Patent Registration No. 4,424,946.
(Patent document 2) European Patent Registration No. 0,201,623.
(Patent document 3) US Patent Publication No. 2009-0176740.

Non-Patent Documents (Non-patent document 1) Minetto M A, Holobar A, Butter A, Farina D. Origin and development of muscle cramps. 2013 Exerc Sport Sci Rev 2013: 41: 3-10.

(Non-patent document 2) Allen R E, Kirby K A. Nocturnal leg cramps. *Am Fam Physician*. 2012: 86(4): 350-5.

(Non-patent document 3) Hensley J G. Leg cramps and restless legs syndrome during pregnancy. J Midwifery Womens Health. 2009: 54(3): 211-218.

(Non-patent document 4) Baltodano N, Gallo B V Weidler D J. Verapamil vs quinine in recumbent nocturnal leg cramps in the elderly. *Arch Int Med* 1988: 148: 1969-1970.

(Non-patent document 5) Voon W C, Sheu S H. Diltiazem for nocturnal leg cramps. Age Ageing 2001: 30: 91-92.

(Non-patent document 6) Stern F H. Value of carisoprodol (Soma) in relieving leg cramps. *J Am Geriatr Soc* 1963: 11:1008-1013.

(Non-patent document 7) Popkin R J. Orphenadrine citrate (Norflex) for the treatment of "restless legs" and related syndromes. *J Am Geriatr Soc* 1971: 19: 76-79.

(Non-patent document 8) Chan P, Huang T Y, Chen Y J, Huang W P, Liu Y C. Randomized, double-blind, placebo-controleed study of the safety and efficacy of vitamin B complex in the treatment of nocturnal leg cramps in elderly patients with hypertension. *J Clin Pharmacol* 1998: 38: 1151-1154.

(Non-patent document 9) Guay D R. Are there alternatives to the use of quinine to treat nocturnal leg cramps? Consult Pharm. 2008: 23(2): 141-56.

(Non-patent document 10) Katzberg H D, Khan A H, So Y T. Assessment: symptomatic treatment for muscle cramps (an evidence-base review): report of the therapeutics and technology assessment subcommittee of the American Academy of Neurology. Neurobiology 2010: 74(8): 691-696.

(Non-patent document 11) Prateepavanich P, Kupnirattsaikul V, Charoensak T. The relationship nbetween myofascial trigger points of gastrocnemius muscle and nocturnal calf cramps. *J Med* Assoc Thai 1999: 82: 451-459.

(Non-patent document 12) Kim D H, Yoon D M, Yoon K B. The effect of myofascial trigger point injections on nocturnal calf cramps. *J Am* Board Fam Med 2015: 28: 21-27.

(Non-patent document 13) Park S J, Yoon K B, Yoon D K, Kim S H. Botulnum toxin treatment for nocturnal calf cramps in patients with lumbar spinal stenosis: a randomized clinical trial. *Arch Phys Med Rehabil* 2017: 98(5): 957-963.

(Non-patent document 14) Farrar J T, Young J P, LaMoreaux L, Werth J L, Poole R M. Clinical importance of changes in chronic pain intensity measured on an 11-point numerical pain rating scale. *Pain* 94(2):149-158 (2001).

(Non-patent document 15) Rowbotham M C. What is a "clinically meaningful" reduction in pain?. *Pain* 94(2): 131-132 (2001).

(Non-patent document 16) Hawker G A, Mian A, Kendzerska T, French M. Measures of adult pain. Arthritis Care Res. 63(S11): S240-S252 (2011).

BRIEF SUMMARY OF THE INVENTION

The present disclosure is directed to providing a pharmaceutical composition for treating or preventing muscle cramps, which is capable of treating or preventing muscle cramps in short time with few side effects.

The present disclosure is also directed to providing a health functional food composition for improving muscle cramps, which is capable of improving muscle cramps in short time with few side effects.

The present disclosure is also directed to providing a method for treating muscle cramps, which is capable of treating muscle cramps in short time with few side effects.

The present disclosure is also directed to providing a novel use of choline alfoscerate for preparing a medication for treating muscle cramps.

The present disclosure relates to a pharmaceutical composition for treating or preventing muscle cramps, which contains choline alfoscerate as an active ingredient.

The pharmaceutical composition may further contain a pharmaceutically acceptable carrier.

The pharmaceutical composition may be for intravenous administration or oral administration.

The daily administration dosage of the pharmaceutical composition may be 1-400 mg/kg body weight based on choline alfoscerate.

The present disclosure also relates to a health functional food composition for improving muscle cramps, which contains choline alfoscerate as an active ingredient.

The present disclosure also relates to a method for treating muscle cramps, which includes administering an effective amount of choline alfoscerate to a patient with muscle cramps.

In the method for treating muscle cramps, the administration may be intravenous administration or oral administration.

In the method for treating muscle cramps, the daily administration dosage may be 1-400 mg/kg body weight based on choline alfoscerate.

The present disclosure also relates to a use of choline alfoscerate for preparing a medication for treating muscle cramps.

The medication may further contain a pharmaceutically acceptable carrier.

The medication may be for intravenous administration or oral administration.

The daily administration dosage of the medication may be 1-400 mg/kg body weight based on choline alfoscerate.

DETAILED DESCRIPTION

Choline alfoscerate is a drug used to improve cerebrovascular diseases and brain metabolism. It is a drug with proven safety, which has no effect on the kidney and liver and with no severe side effect reported. When administered to a patient with muscle cramps, it can significantly reduce pain and the occurrence of muscle cramps. Accordingly, it may be used as an active ingredient in a pharmaceutical composition for treating or preventing muscle cramps and a health functional food composition for improving muscle cramps and may also be used for a method for treating muscle cramps by administering choline alfoscerate. In addition, choline alfoscerate may also be used to prepare a medication for treating muscle cramps.

The present disclosure relates to a pharmaceutical composition for treating or preventing muscle cramps, which contains choline alfoscerate as an active ingredient.

The present disclosure also relates to a health functional food composition for improving or preventing muscle cramps, which contains choline alfoscerate as an active ingredient.

The present disclosure also relates to method for treating muscle cramps by administering an effective amount of choline alfoscerate to a patient with muscle cramps.

The present disclosure also relates to a use of choline alfoscerate for preparing a medication for treating muscle cramps.

The pharmaceutical composition for treating or preventing muscle cramps of the present disclosure may be prepared into a formulation for intravenous administration or oral administration. The formulation may contain a pharmaceutically acceptable carrier commonly used to prepare a pharmaceutical composition.

The carrier may include various compounds or mixtures, including lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc.

For the preparation, a commonly used diluent or excipient such as a filler, an extender, a binder, a humectant, a disintegrant, a surfactant, etc. may be used.

A solid formulation for oral administration may be prepared by mixing the choline alfoscerate with at least one carrier, e.g., starch, calcium carbonate, sucrose, lactose, gelatin, etc. In addition to the simple carriers, a lubricant such as magnesium stearate or talc may also be used.

A liquid formulation for oral administration, which may be a suspension, an internal solution, an emulsion, a syrup, etc., may contain, in addition to commonly used simple diluents such as water or liquid paraffin, various excipients such as a humectant, a sweetener, an aromatic, a preservative, etc.

A formulation for intravenous administration includes a sterilized aqueous solution, a non-aqueous solution, a suspension, an emulsion and a freeze-dried formulation. As the non-aqueous solution or suspension, propylene glycol, polyethylene glycol, a vegetable oil such as olive oil, an injectable ester such as ethyl oleate, etc. may be used.

The administration dosage of the pharmaceutical composition for treating or preventing muscle cramps of the present disclosure varies depending on the physical condition and body weight of a patient, the severity of a disease, drug type, administration route and administration period but may be determined adequately by those skilled in the art.

In order to achieve the desired effect, the daily administration dosage may be 1-400 mg/kg body weight, specifically 2-200 mg/kg, based on choline alfoscerate. The administration may be made once or several times a day. In addition, the administration may be made periodically over 1-4 weeks. Most specifically, the formulation for oral administration may be administered once or 2-3 times at a daily dosage of 5-200 mg/kg body weight and the formulation for intravenous administration may be administered 1-3 times over 1-4 weeks a daily dosage of 2-50 mg/kg. However, the scope of the present disclosure is not limited by the dosage or frequency of the administration.

The pharmaceutical composition for treating or preventing muscle cramps of the present disclosure may be administered to mammals including rat, mouse, livestock, human, etc. via various routes. For example, it may be administered orally or via intravenous injection.

The present disclosure also relates to a health functional food composition for improving muscle cramps, which contains choline alfoscerate as an active ingredient.

When choline alfoscerate is used as an active ingredient of a health functional food, it may be used together with other foods or food ingredients adequately according to common methods. The mixing amount of the active ingredient may be determined adequately depending on purposes such as improvement, prevention, etc.

In general, the health functional food according to the present disclosure may contain choline alfoscerate in an amount of 15 parts by weight or less, specifically 10 parts by weight or less, more specifically 5 parts by weight or less. However, for the purpose of long-term intake for improvement, prevention or health care, the amount may be smaller. In addition, because the safety of choline alfoscerate is proven for long-term oral administration, a larger amount may also be used.

The type of the health functional food is not particularly limited and the choline alfoscerate may be contained in any food in the usual sense, including meat, sausage, bread, chocolate, candies, snacks, confectionery, pizza, instant and other noodles, gums, dairy products including ice creams, soups, beverages, tea, drinks, alcoholic beverages, vitamin complexes, etc.

When the health functional food is in the form of a drink, it may further contain various flavorants or natural carbohydrates as common drinks. The natural carbohydrate may be a monosaccharide such as glucose or fructose, a disaccharide such as maltose or sucrose, a polysaccharide such as dextrin or cyclodextrin or a sugar alcohol such as xylitol, sorbitol, erythritol, etc. As a sweetener, a natural sweetener such as thaumatin or *stevia* extract, a synthetic sweetener such as saccharin or aspartame, etc. may be used. The content of the natural carbohydrate may be about 0.01-0.04 g, specifically about 0.02-0.03 g, per 100 mL of the drink.

In addition, the health functional food composition for improving muscle cramps, which contains choline alfoscerate as an active ingredient, may further contain various nutrients, vitamins, electrolytes, flavors, colorants, pectic acid and its salts, alginic d and its salts, organic acids, protective colloidal thickeners, pH control agents, stabilizers, antiseptics, glycerin, alcohols and carbonating agents used in carbonated drinks. In addition, it may contain a pulp used for preparing natural fruit juice, fruit juice drinks and vegetable drinks. These ingredients may be used either independently or in combination. The content of these additives is usually 0.01-0.1 part by weight based on 100 parts by weight of the composition of the present disclosure, although not being limited thereto.

EXAMPLES

Hereinafter, the present disclosure will be described in detail through examples. However, the following examples are for illustrative purposes only and it will be apparent to those of ordinary skill in the art that the scope of the present disclosure is not limited by the examples.

1. Characterization and Classification of Patients

Patients who experience muscle cramps when stabilized for 3 months without taking exercise were selected as subjects. The patients were asked to report the characteristics of muscle cramps (site of occurrence, time of occurrence, frequency of occurrence and pain intensity), causative factors of muscle cramps, presence and of diseases relationship with muscle cramps, relationship between muscle cramps and drug medication, medication of therapeutic agents for muscle cramps, etc.

The characteristics of "trigger point injection group (control group)" patients are described in Table 1, the characteristics of "choline alfoscerate intravenous administration group (Example 1)" patients are described in Table 2 and the characteristics of "choline alfoscerate oral administration group (Example 2) patients are described in Table 3.

TABLE 1

| Patient number | Gender | Age | Period (years) of muscle cramps | Site of muscle cramps |
|---|---|---|---|---|
| 1 | M | 78 | 10 | Lower leg |
| 2 | F | 79 | 3 | Lower leg |
| 3 | M | 72 | 1 | Lower leg |
| 4 | M | 63 | 1 | Lower leg |
| 5 | F | 82 | 1 | Lower leg |
| 6 | M | 63 | 1 | Lower leg |
| 7 | M | 64 | 1 | Lower leg |
| 8 | F | 78 | 1 | Lower leg |
| 9 | F | 70 | 1 | Lower leg |
| 10 | F | 78 | 1 | Lower leg |
| 11 | F | 62 | 0.5 | Lower leg |
| 12 | F | 64 | 1 | Lower leg |
| 13 | F | 65 | 1 | Lower leg |
| 14 | M | 74 | 1 | Lower leg |
| 15 | M | 69 | 1 | Hand |
| 16 | F | 77 | 1 | Lower leg |
| 17 | F | 67 | 1 | Hand |
| 18 | F | 66 | 1 | Lower leg |
| 19 | M | 65 | 1 | Lower leg |
| 20 | F | 56 | 1 | Lower leg |
| 21 | F | 57 | 3 | Lower leg |
| 22 | F | 47 | 2 | Hand |
| 23 | M | 61 | 3 | Lower leg |
| 24 | F | 84 | 2 | Lower leg |
| 25 | M | 77 | 5 | Lower leg |
| 26 | M | 39 | 1 | Lower leg |
| 27 | F | 51 | 0.5 | Lower leg |
| 28 | F | 76 | 4 | Lower leg |
| 29 | F | 46 | 1 | Lower leg |
| 30 | M | 72 | 3 | Lower leg |
| 31 | F | 72 | 2.5 | Lower leg |
| 32 | F | 65 | 2 | Lower leg |
| 33 | F | 52 | 2 | Lower leg |
| 34 | F | 46 | 2 | Lower leg |
| 35 | F | 84 | 5 | Lower leg |
| 36 | F | 51 | 2 | Lower leg |
| 37 | F | 58 | 2 | Lower leg |
| 38 | F | 44 | 1 | Lower leg |
| 39 | M | 61 | 2 | Lower leg |
| 40 | F | 64 | 3 | Lower leg |
| 41 | M | 58 | 2 | Lower leg |
| 42 | M | 63 | 3 | Lower leg and hand |
| 43 | F | 72 | 3 | Lower leg |
| 44 | M | 75 | 1 | Lower leg |
| 45 | M | 52 | 1 | Lower leg |
| 46 | M | 51 | 1.5 | Lower leg |
| 47 | F | 76 | 4 | Lower leg |
| 48 | M | 56 | 1 | Hand |
| 49 | M | 72 | 3 | Lower leg |
| 50 | M | 73 | 3 | Lower leg |
| 51 | M | 65 | 2 | Lower leg |
| 52 | F | 66 | 2 | Lower leg |
| 53 | F | 46 | 2 | Lower leg |
| 54 | F | 87 | 5 | Lower leg and hand |
| 55 | F | 61 | 2 | Lower leg |
| 56 | F | 61 | 2 | Lower leg |
| 57 | F | 54 | 1 | Lower leg |
| 58 | M | 61 | 5 | Thigh |
| 59 | M | 58 | 2 | Lower leg |
| 60 | F | 74 | 3 | Lower leg |
| 61 | M | 61 | 5 | Hand |
| Mean ± SD | | 64.6 ± 11.1 | 2.16 ± 1.60 | |

TABLE 2

| Patient number | Gender | Age | Period (years) of muscle cramps | Site of muscle cramps |
|---|---|---|---|---|
| 1 | M | 58 | 1 | Lower leg |
| 2 | F | 50 | 1 | Lower leg |
| 3 | F | 64 | 1 | Lower leg |
| 4 | M | 76 | 1 | Lower leg |
| 5 | F | 58 | 1 | Lower leg |
| 6 | F | 36 | 1 | Lower leg |
| 7 | F | 56 | 1 | Lower leg |
| 8 | F | 55 | 1 | Lower leg |
| 9 | F | 55 | 1 | Lower leg |
| 10 | M | 54 | 1 | Lower leg |
| 11 | F | 62 | 1 | Lower leg |
| 12 | M | 71 | 1 | Lower leg |
| 13 | M | 79 | 1 | Lower leg |
| 14 | F | 51 | 1 | Lower leg |
| 15 | F | 63 | 1 | Lower leg |
| 16 | F | 75 | 1 | Lower leg |
| 17 | M | 63 | 1 | Lower leg |
| 18 | F | 73 | 1 | Lower leg |
| 19 | F | 65 | 1 | Lower leg |
| 20 | F | 55 | 1 | Lower leg |
| 21 | M | 71 | 1 | Lower leg |
| 22 | M | 62 | 1 | Lower leg |
| 23 | F | 58 | 1 | Lower leg |
| 24 | M | 52 | 1 | Lower leg |
| 25 | F | 79 | 1 | Lower leg |
| 26 | F | 74 | 1 | Hand and foot |
| 27 | F | 51 | 1 | Lower leg |
| 28 | F | 55 | 1 | Lower leg |
| 29 | F | 55 | 1 | Lower leg |
| 30 | F | 69 | 3 | Lower leg |
| 31 | M | 55 | 1 | Lower leg |
| 32 | F | 87 | 3 | Lower leg |
| 33 | M | 59 | 5 | Lower leg |
| 34 | M | 64 | 5 | Lower leg |
| 35 | F | 57 | 3 | Lower leg |
| 36 | M | 72 | 3 | Hand and foot |
| 37 | F | 54 | 2 | Lower leg |
| 38 | F | 66 | 3 | Lower leg |
| 39 | M | 56 | 5 | Hand |
| 40 | F | 60 | 5 | Lower leg |
| 41 | M | 77 | 3 | Lower leg |
| 42 | F | 64 | 7 | Lower leg |
| 43 | M | 59 | 2 | Lower leg |
| 44 | M | 60 | 2 | Lower leg |
| 45 | F | 67 | 3 | Lower leg |
| 46 | M | 55 | 3 | Lower leg |
| 47 | M | 63 | 5 | Lower leg |
| 48 | F | 57 | 3 | Lower leg |
| 49 | M | 84 | 3 | Lower leg |
| 50 | F | 54 | 2 | Lower leg |
| 51 | F | 71 | 3 | Lower leg |
| 52 | M | 56 | 3 | Hand |
| 53 | M | 60 | 3 | Lower leg |
| 54 | M | 77 | 3 | Lower leg |
| 55 | M | 64 | 5 | Lower leg |
| 56 | F | 58 | 1 | Lower leg |
| 57 | M | 63 | 2 | Lower leg |
| 58 | M | 65 | 1 | Forearm |
| 59 | M | 78 | 2 | Lower leg |
| 60 | F | 79 | 1 | Thigh |
| 61 | F | 55 | 1 | Lower leg |
| 62 | M | 73 | 3 | Lower leg |
| 63 | F | 57 | 2 | Lower leg |
| 64 | F | 69 | 3 | Lower leg |
| 65 | M | 55 | 1 | Lower leg |
| 66 | F | 87 | 3 | Lower leg |
| 67 | M | 59 | 5 | Lower leg |
| 68 | M | 64 | 5 | Lower leg |
| Mean ± SD | — | 63.3 ± 9.89 | 2.16 ± 1.48 | — |

TABLE 3

| Patient number | Gender | Age | Period (years) of muscle cramps | Site of muscle cramps |
|---|---|---|---|---|
| 1 | M | 73 | 1 | Lower leg |
| 2 | M | 53 | 0.5 | Lower leg |
| 3 | F | 57 | 1 | Lower leg |
| 4 | F | 67 | 1 | Lower leg |
| 5 | F | 55 | 1 | Lower leg |
| 6 | F | 68 | 1 | Lower leg |
| 7 | F | 78 | 1 | Hand and foot |
| 8 | M | 51 | 0.5 | Foot |
| 9 | M | 80 | 3 | Hand and foot |
| 10 | M | 79 | 1 | Hand and foot |
| 11 | F | 56 | 1 | Hand and foot |
| 12 | M | 74 | 3 | Face |
| 13 | F | 77 | 1 | Lower leg |
| 14 | F | 55 | 1 | Lower leg |
| 15 | F | 53 | 5 | Lower leg |
| 16 | M | 44 | 3 | Lower leg |
| 17 | M | 65 | 2 | Lower leg |
| 18 | M | 82 | 5 | Lower leg |
| 19 | F | 72 | 5 | Lower leg and hand |
| 20 | F | 63 | 5 | Lower leg |
| 21 | M | 42 | 3 | Lower leg |
| 22 | F | 61 | 3 | Lower leg |
| 23 | M | 47 | 3 | Lower leg |
| 24 | M | 58 | 3 | Lower leg |
| 25 | M | 46 | 1 | Hand and foot |
| 26 | F | 74 | 3 | Hand |
| 27 | M | 53 | 1 | Waist |
| 28 | F | 59 | 2 | Thigh |
| 29 | F | 57 | 2 | Hand |
| 30 | F | 63 | 3 | Lower leg |
| 31 | M | 63 | 2 | Hand |
| 32 | M | 55 | 1 | Lower leg |
| 33 | F | 63 | 1 | Lower leg |
| 34 | M | 64 | 1 | Lower leg |
| 35 | F | 66 | 1.5 | Lower leg |
| 36 | F | 67 | 1 | Lower leg |
| 37 | F | 58 | 1 | Lower leg |
| 38 | F | 55 | 1 | Lower leg |
| 39 | F | 72 | 2 | Lower leg |
| 40 | F | 78 | 1 | Hand and foot |
| 41 | M | 51 | 2 | Foot |
| 42 | F | 74 | 2 | Foot |
| 43 | M | 79 | 1 | Lower leg |
| 44 | F | 66 | 1 | Hand and foot |
| 45 | F | 74 | 3 | Arm |
| 46 | F | 77 | 1 | Lower leg |
| 47 | M | 44 | 1 | Lower leg |
| 48 | M | 63 | 5 | Lower leg |
| 49 | M | 44 | 3 | Lower leg |
| 50 | F | 67 | 2 | Lower leg |
| 51 | M | 76 | 5 | Lower leg |
| 52 | M | 75 | 3 | Lower leg and hand |
| 53 | F | 53 | 2 | Lower leg |
| 54 | M | 42 | 3 | Lower leg |
| 55 | M | 61 | 3 | Lower leg |
| 56 | M | 56 | 3 | Lower leg |
| 57 | M | 58 | 3 | Lower leg |
| 58 | M | 68 | 1 | Hand and foot |
| 59 | F | 74 | 2 | Hand |
| 60 | M | 53 | 1 | Lower leg |
| 61 | F | 59 | 2 | Hand |
| 62 | F | 57 | 2 | Hand |
| 63 | F | 63 | 3 | Lower leg |
| 64 | F | 69 | 1 | Lower leg |
| Mean ± SD | — | 62.6 ± 10.7 | 2.09 ± 1.27 | — |

The number of the patients was 193, 86 male and 107 female. The average age was 63.5 years and the average period of muscle cramps was 2.14 years.

The number of the "trigger point injection group (control group)" patients was 61, 25 male and 36 female. The average age was 64.6±11.1 years and the average period of muscle cramps was 2.16±1.60 years. The muscle cramps occurred in the lower leg for 53 people, in the hand for 5 people, in the lower leg and hand for 2 people and in the thigh for one person.

The number of the "choline alfoscerate intravenous administration group (Example 1)" patients was 68, 31 male and 37 female. The average age was 63.3±9.89 years and the average period of muscle cramps was 2.16±1.48 years. The muscle cramps occurred in the lower leg for 62 people, in the hand for 2 people, in the hand and foot for 2 people and in the arm and thigh respectively for one person.

The number of the "choline alfoscerate oral administration group (Example 2)" patients was 64, 30 male and 34 female. The average age was 62.6±10.7 years and the average period of muscle cramps was 2.09±1.27 years. The muscle cramps occurred in the lower leg for 41 people, in the hand and foot for 8 people, in the hand for 6 people, in the foot for 3 people, in the lower leg and hand for 2 people and in the face, waist, thigh and arm respectively for one person.

2. Treatment of Test Groups

The "trigger point injection group (control group)" patients were injected with 5 mL of 0.5% lidocaine at the trigger points (4-5 points), once a week.

The "choline alfoscerate intravenous administration group (Example 1)" patients were intravenously injected slowly with choline alfoscerate (1 g/4 mL) mixed in 100 mL of physiological saline, twice a week.

The "choline alfoscerate oral administration group (Example 2)" patients were injected with choline alfoscerate (400 mg/capsule), 3 times a day.

3. Test Method

The test period was one month. The former two weeks was denoted as T1 and the latter two weeks was denoted as T2. Pain intensity and frequency of cramps for a week were measured. The pain intensity was evaluated according to the 11-point pain intensity numerical rating scale (PI-NRS), where 0=no pain, weakest pain=1 and most severe pain=10. 2-point reduction in the pain intensity was considered clinically significant as reported (Farrar 2001, Rowbotham 2001, Hawker 2011). The pain intensity was measured on the first visit and was compared with the pain intensity 2 weeks (T1) and 4 weeks (T2) after the first drug administration.

For the frequency of muscle cramps, the frequency of muscle cramps for a week before the first drug administration was compared with the frequency of muscle cramps for a week before the visit on the weeks 2 and 4.

Statistical analysis was conducted using the SASS package ver. 23 and significance was tested by the paired t-test.

4. Test Result

The therapeutic effect for muscle cramps for the "trigger point injection group (control group)", the "choline alfoscerate intravenous administration group (Example 1)" and the "choline alfoscerate oral administration group (Example 2)" is shown in Table 4.

TABLE 4

| | | Before drug administration | T1 (first 2 weeks) | T2 (second 2 weeks) |
|---|---|---|---|---|
| Control group (TPI) | Pain intensity | 5.34 ± 0.87 | 3.74 ± 0.91* | 2.11 ± 0.76* |
| | Frequency of muscle cramps | 2.84 ± 0.99 | 2.00 ± 0.68* | 1.43 ± 0.53* |
| Example 1 (choline alfoscerate, intravenous) | Pain intensity | 6.50 ± 1.26 | 2.56 ± 1.49*# | 1.32 ± 0.91*# |
| | Frequency of muscle cramps | 4.91 ± 2.40 | 1.56 ± 1.34*# | 0.88 ± 1.19*# |

TABLE 4-continued

|  |  | Before drug administration | T1 (first 2 weeks) | T2 (second 2 weeks) |
|---|---|---|---|---|
| Example 2 (choline alfoscerate, oral) | Pain intensity | 6.31 ± +0.94 | 3.94 ± 1.17* | 1.88 ± 0.92* |
|  | Frequency of muscle cramps | 5.25 ± 1.47 | 2.67 ± 1.07*# | 1.05 ± 0.70*# |

*$P < 0.05$: significant difference at T1 or T2 from as compared to before drug administration (trigger point injection, choline alfoscerate intravenous administration or choline alfoscerate oral administration)
$P < 0.05$: significant difference of Example 1 or Example 2 as compared to control group at T1 or T2

The pain intensity decreased significantly for the "trigger point injection group (control group)", from 5.34 points before drug administration to 3.74 points at 2 weeks after the first drug administration (T1) and to 2.11 points at the second 2 weeks, i.e., at 4 weeks after the first drug administration (T2). For the "choline alfoscerate intravenous administration group (Example 1)", the pain intensity decreased significantly from 6.50 points before drug administration to 2.56 points at T1 and to 1.32 points at T2. For the "choline alfoscerate oral administration group (Example 2)", the pain intensity decreased significantly from 6.31 points before drug administration to 3.94 points at T1 and to 1.88 points at T2.

The "choline alfoscerate intravenous administration group (Example 1)" showed significant decrease in the pain intensity as compared to the "trigger point injection group (control group)" at both T1 and T2.

The frequency of muscle cramps for a week decreased significantly for the "trigger point injection group (control group)", from 2.84 times before drug administration to 2.00 times at T1 and to 1.43 times at T2. For the "choline alfoscerate intravenous administration group (Example 1)", it decreased significantly from 4.91 times before drug administration to 1.56 times at T1 and to 0.88 time at T2. For the "choline alfoscerate oral administration group (Example 2)", it decreased significantly from 5.25 times before drug administration to 2.67 times at T1 and to 1.05 times at T2.

The "choline alfoscerate intravenous administration group (Example 1)" showed significant decrease in the frequency of muscle cramps for a week as compared to the "trigger point injection group (control group)" at T1. The "choline alfoscerate oral administration group (Example 2)" showed significant increase in the frequency of muscle cramps for a week as compared to the "trigger point injection group (control group)" at T1.

In addition, the "choline alfoscerate intravenous administration group (Example 1)" and the "choline alfoscerate oral administration group (Example 2)" showed significant decrease in the frequency of muscle cramps as compared to the "trigger point injection group (control group)" at T2.

The reason why the "choline alfoscerate oral administration group (Example 2)" showed higher frequency of muscle cramps for a week as compared to the "trigger point injection group (control group)" at T1 may be because the patients of the "choline alfoscerate oral administration group (Example 2)" had much higher frequency of muscle cramps before the drug administration. Despite this difference in patients, the frequency of muscle cramps for a week decreased significantly as compared to the "trigger point injection group (control group)" at T2.

Both the "choline alfoscerate intravenous administration group (Example 1)" and the "choline alfoscerate oral administration group (Example 2)" showed remarkably decreased pain intensity and frequency of muscle cramps and some patients reported that the muscle cramps disappeared the next day after the drug administration. In addition, the patients showed higher compliance to the intravenous injection than the injection directly to the site of muscle cramps.

The "choline alfoscerate intravenous administration group (Example 1)" and the "choline alfoscerate oral administration group (Example 2)" showed no side effect after the treatment. Because choline alfoscerate has no effect on the kidney and liver, it is thought that it can be used for people with kidney or liver problems as a therapeutic agent for muscle cramps.

Hereinafter, the preparation examples of a pharmaceutical composition for treating or preventing muscle cramps or a health functional food composition for improving muscle cramps, which contains choline alfoscerate as an active ingredient, of the present disclosure are described. However, the examples are provided as specific examples only and are not intended to limit the present disclosure.

| Preparation Example 1: Preparation of tablet | |
|---|---|
| Choline alfoscerate | 10 mg |
| Corn starch | 100 mg |
| Lactose | 100 mg |
| Magnesium stearate | 2 mg |

After mixing the above ingredients, a tablet was prepared according to a common tablet making method.

| Preparation Example 2: Preparation of capsule | |
|---|---|
| Choline alfoscerate | 10 mg |
| Crystalline cellulose | 3 mg |
| Lactose | 14.8 mg |
| Magnesium stearate | 0.2 mg |

After mixing the above ingredients, a capsule was prepared by filling the mixture in a gelatin capsule according to a common method.

| Preparation Example 3: Preparation of injection | |
|---|---|
| Choline alfoscerate | 10 mg |
| Mannitol | 180 mg |
| Sterilized distilled water for injection | 2974 mg |
| $Na_2HPO_4 \cdot 12H_2O$ | 26 mg |

An injection was prepared by a common injection preparation method according to the above composition per ampoule.

| Preparation Example 4: Preparation of liquid formulation | |
|---|---|
| Choline alfoscerate | 20 mg |
| High-fructose corn syrup | 10 g |
| Mannitol | 5 g |
| Purified water | adequate |

The above ingredients were dissolved by adding to purified water according to a common liquid formulation preparation method. After adding an adequate amount of lemon flavor, purified water was added to make the total volume 100 mL and the resulting mixture was filled in a brown bottle and then sterilized.

| | |
|---|---|
| Choline alfoscerate | 100 mg |
| Vitamin mixture | adequate |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | adequate |
| Ferrous sulfate | 1.75 mg |
| Zinc oxide | 0.82 mg |
| Magnesium carbonate | 25.3 mg |
| Potassium phosphate, monobasic | 15 mg |
| Calcium phosphate, dibasic | 55 mg |
| Potassium citrate | 90 mg |
| Calcium carbonate | 100 mg |
| Magnesium chloride | 24.8 mg |

The above contents of the vitamin and mineral mixtures are given as specific examples relatively suitable for health functional food but may be varied as desired. A health functional food composition was prepared by a common method after mixing the above ingredients and preparing into a granule.

| Preparation Example 6: Preparation of drink-type health functional food | |
|---|---|
| Choline alfoscerate | 100 mg |
| Citric acid | 1,000 mg |
| Oligosaccharide | 100 g |
| Plum concentrate | 2 g |

| Preparation Example 6: Preparation of drink-type health functional food | |
|---|---|
| Taurine | 1 g |
| Purified water | to 900 mL |

According to a common health functional drink preparation method, the above ingredients were mixed and heated at 85° C. for about 1 hour under stirring. The resulting solution was filtered, collected in a sterilized 2-L container and stored in a refrigerator after sealing and sterilization for use in the preparation of the health functional drink of the present disclosure.

Because choline alfoscerate can significantly reduce pain and the occurrence of muscle cramps when administered to a patient with muscle cramps, it may be used as an active ingredient in a pharmaceutical composition for treating or preventing muscle cramps and a health functional food composition for improving muscle cramps and may also be used for a method for treating muscle cramps by administering choline alfoscerate. In addition, choline alfoscerate may also be used to prepare a medication for treating muscle cramps.

The invention claimed is:

1. A method for treating muscle cramps, comprising administering an effective amount of choline alfoscerate to a patient with muscle cramps.

2. The method for treating muscle cramps according to claim 1, wherein the administration is intravenous administration or oral administration.

3. The method for treating muscle cramps according to claim 1, wherein the daily administration dosage is 1-400 mg/kg body weight based on choline alfoscerate.

* * * * *